(12) United States Patent
Sharratt et al.

(10) Patent No.: US 7,034,190 B2
(45) Date of Patent: Apr. 25, 2006

(54) PROCESS FOR THE PRODUCTION OF FLUOROMETHYL HEXAFLUOROISOPROPYL ETHER

(75) Inventors: Andrew Paul Sharratt, Cheshire (GB); Lee Colin Draper, Flintshire (GB)

(73) Assignee: Ineos Fluor Holdings Limited, Runcorn (GB)

( * ) Notice: Subject to any disclaimer, the term of this patent is extended or adjusted under 35 U.S.C. 154(b) by 0 days.

(21) Appl. No.: 10/451,266

(22) PCT Filed: Dec. 21, 2001

(86) PCT No.: PCT/GB01/05728

§ 371 (c)(1),
(2), (4) Date: Dec. 9, 2003

(87) PCT Pub. No.: WO02/50003

PCT Pub. Date: Jun. 27, 2002

(65) Prior Publication Data

US 2004/0073070 A1    Apr. 15, 2004

(30) Foreign Application Priority Data

Dec. 21, 2000  (GB) ..................... 0031301

(51) Int. Cl.
*C07C 41/00*    (2006.01)
(52) U.S. Cl. ..................................... 568/683; 568/682
(58) Field of Classification Search ................ 568/683, 568/682
See application file for complete search history.

(56) References Cited

U.S. PATENT DOCUMENTS

| 4,250,334 A | 2/1981 | Coon et al. ................. 568/683 |
| 5,504,263 A | 4/1996 | Burgess et al. ............. 570/142 |
| 5,696,308 A | 12/1997 | Burgess et al. ............. 570/142 |
| 5,750,807 A | 5/1998 | Burgess et al. ............. 570/142 |
| 5,990,359 A | 11/1999 | Ryan et al. ................. 568/683 |

FOREIGN PATENT DOCUMENTS

| WO | WO 93/12057 | 6/1993 |
| WO | WO 97/25303 | 7/1997 |

*Primary Examiner*—Rosalynd Keys
(74) *Attorney, Agent, or Firm*—Morgan Lewis & Bockius LLP

(57) ABSTRACT

A process for the production of fluoromethylhexafluoroisopropylether which comprises contacting bis(fluoromethyl) ether with hexafluoroisopropyl alcohol in which the molar ratio of the ether to alcohol is in excess of 2:1. The reaction takes place in the presence of a molar ratio of acid to hexafluoroisopropyl alcohol of 2:1 to 10:1.

12 Claims, No Drawings

PROCESS FOR THE PRODUCTION OF FLUOROMETHYL HEXAFLUOROISOPROPYL ETHER

This application is a 371 of PCT/GB 01/05728 filed Dec. 21, 2001.

This invention relates to a process for the production of fluoromethylhexafluoroisopropylether of formula $CH_2FOCH(CF_3)_2$, which has anaesthetic properties and is known as "Sevoflurane".

Several processes have been proposed for the production of Sevoflurane including the reaction of hexafluoroisopropyl alcohol, $(CF_3)_2CHOH$ (HFIP) with formaldehyde and hydrogen fluoride. U.S. Pat. No. 4,250,334 describes a process in which hexafluoroisopropyl alcohol is added to a mixture of a stoichiometric excess of paraformaldehyde and hydrogen fluoride plus sufficient sulphuric acid to sequester most of the water formed at a temperature. The mixture is maintained at a temperature above 57° C. By operating at this elevated temperature, Sevoflurane vapour is generated from the reaction mixture and is then collected and condensed. U.S. Pat. No. 4,469,898 also describes a process in which hexafluoroisopropyl alcohol is mixed with formaldehyde, hydrogen fluoride and a dehydrating agent such as sulphuric acid. A reaction temperature of at least 50° C. is said to improve product yields and a temperature range of 57 to 70° C. is preferred.

Operating processes at elevated temperature, especially with chemically aggressive species may cause corrosion of the plant unless steps are taken to avoid or reduce this, for example, by employing certain materials of construction. Such steps may provide a technical remedy but introduce additional capital cost. In addition, such processes may lead to the formation of significant proportion of by-products or unreacted feedstock, for example HFIP. These components may present difficulties in purifying and separating the desired product. For example WO 99144978 describes a process to remove HFIP from crude Sevoflurane and involves employing an aqueous alkaline wash and several process stages so providing a complicated purification process which increases costs and requires a high level of process control.

A process for producing an alpha-fluoroether such as and including Sevoflurane is described in International Patent Publication No. WO 93/12057, the process comprising reacting a non-enolisable aldehyde such as formaldehyde with hydrogen fluoride to form an intermediate and reacting the intermediate with an alcohol such as hexafluoroisopropyl alcohol to form an alpha-fluoroether such as Sevoflurane. The production of Sevoflurane by adding hexafluoroisopropyl alcohol to the reaction mixture derived from trioxane (as the source of formaldehyde) and hydrogen fluoride and containing the intermediate bis(fluoromethyl) ether is described in Example 19.

As is described in WO 93112057, the reaction products obtained in Example 19 comprised mainly unreacted hexafluoroisopropyl alcohol and unreacted bis(fluoromethyl) ether (BFME) and the yield of Sevoflurane was low. Accordingly the process is unsuitable or at best barely suitable for industrial application even with recovery and recycle of unreacted hexafluoroisopropyl alcohol and bis (fluoromethyl) ether.

WO97/25303 describes a process for the production of Sevoflurane in which essentially pure bis(fluoromethyl) ether is reacted with hexafluoroisopropyl alcohol. Good yields of Sevoflurane are reported in WO97125303. A process is described in which the reaction may be carried out at ambient temperature and in which the molar ratio of BFME to HFIP is preferably not greater than 2:1 and is usually in the range 0.5:1 to 1.5:1. Furthermore, a large excess of ether is said to be undesirable.

We have now surprisingly found that Sevoflurane may be produced in high yield by reacting BFME with HFIP wherein the BFME reactant is present in excess at a level not hitherto contemplated in the art.

According to the present invention there is provided a process for the production of fluoromethylhexafluoroisopropylether which comprises contacting bis(fluoromethyl) ether with hexafluoroisopropyl alcohol wherein the molar ratio of said ether to said alcohol is in excess of 2:1 whereby the ether and alcohol react to produce fluoromethylhexafluoroisopropylether and recovering fluoromethylhexafluoroisopropylether.

The molar ratio of the ether to alcohol reactants is suitably at least 2.5:1 and preferably from 3:1 to 12:1. Optimally the molar ratio of the ether to the alcohol is 3:1 to 10:1. Advantageously, a relatively high level of BFME to HFIP reduces the formation of an undesirable by-product, fluoromethylmethoxy hexafluoroisopropyl ether known as "mono".

Suitably the reaction is carried out in the presence of an acid.

Suitable acids include Lewis acids, for example titanium tetrachloride, aluminium trichloride, aluminium trifluoride and antimony pentafluoride and especially Bronsted acids. Particularly preferred Bronsted acids include hydrogen fluoride, phosphoric acid, fluorosulphonic acid, trifluoromethane sulphonic acid and, more preferably, sulphuric acid and mixtures of two or more of these acids.

In a preferred embodiment, the invention provides a process for the production of fluoromethylhexafluoroisopropylether which comprises contacting bis(fluoromethyl) ether with hexafluoroisopropyl alcohol in the presence of an acid wherein the molar ratio of said ether to said alcohol is in excess of 2:1 whereby the ether and alcohol react to produce fluoromethylhexafluoroisopropylether and recovering fluoromethylhexafluoroisopropylether.

It has been found that a molar excess of acid relative to the level of HFIP and preferably a molar ratio of at least 1.5 moles of acid per mole of HFIP provides improved yields of Sevoflurane and reduced formation of by-products for example, fluoromethylmethoxy hexafluoroisopropyl ether and hexafluoroisopropylmethoxy hexafluoroisopropyl ether, known as "dimer". The molar ratio of acid to HFIP is preferably 2:1 to 10:1, and especially 4:1 to 10:1.

Desirably the molar ratio of BFME to acid is less than 6:1 and preferably less than 4:1 especially at higher ratios of BFME to HFIP, for example greater than 6:1. More preferably the molar ratio of BFME to acid is less than 3. The BFME to acid molar ratio may be less than 1.5 specially where the molar ratio of the BFME to HFIP is less than 3. Suitably the molar ratio of BFME to acid is at least 0.2 and desirably at least 0.5.

The relative quantities of HFIP, BFME and acid are advantageously selected so as to promote the formation of Sevoflurane and the suppression of by-products including mono and dimer. References to moles of acid are calculated on the basis of moles of a dibasic acid, for example sulphuric acid.

Preferably, HFIP is added to the BFME slowly and, suitably, continuously, for example dropwise, and with agitation of the reaction mixture so as to reduce the formation of by-products especially dimer.

In a further preferred embodiment the reaction between BFME and HFIP is conveniently carried out at a temperature of less than 50° C., although higher temperatures for example up to 100° C. may be employed if desired. Suitably the process is carried out at a temperature above 0° C. Preferably the reaction is carried out at a temperature from 10 to 50° C. and especially at a temperature of 10 to 35° C. Conducting the reaction at a temperature of less than 50° C. advantageously reduces or avoids drawbacks associated with processes operated at higher temperatures yet still permits high yields of Sevoflurane to be obtained. In particular, it has been found that a low reaction temperature in the preferred embodiment of the invention provides excellent selectivity as compared to reactions conducted at temperatures over 50° C., with less by-product, for example fluorinated mono and dimer acetals, being formed.

Suitably the process is carried out at atmospheric pressure, although if desired subatmospheric or superatmospheric pressure may be employed.

According to an especially preferred embodiment of the invention there is provided a process for the production of fluoromethylhexafluoroisopropylether which comprises contacting bis(fluoromethyl) ether with hexafluoroisopropyl alcohol in the presence of sulphuric acid at a temperature from 10 to 50° C. wherein the molar ratio of said ether to said alcohol is from 3:1 to 12:1 the molar ratio of the acid to hexafluoroisopropyl alcohol is 2:1 to 10:1 and the molar ratio of BFME to acid is 4:1 to 1:2 whereby the ether and alcohol react to produce fluoromethylhexafluoroisopropylether and recovering fluoromethylhexafluoroisopropylether.

The present invention provides a process in which a high yield of Sevoflurane is obtained and which suitably is at least 30 g Sevoflurane per 100 g HFIP, preferably 40 g and especially at least 50 g of Sevoflurane per 100 g HFIP and may be in excess of 90 g Sevoflurane per 100 g HFIP. The precise operating conditions may be set according to desire depending on other factors for example the level or type of by-products, the process configuration, the nature of downstream processing.

Suitably the contact time for HFIP and BFME to produce Sevoflurane is up to 6 hours and preferably from 1 minute to 6 hours. More preferably the contact time is from 10 to 60 minutes, especially 15 to 45 minutes. The contact time is suitably selected according to whether the process is operated on a continuous or batch basis.

The bis(fluoromethyl) ether is conveniently and preferably produced by the reaction of formaldehyde or a source of formaldehyde with hydrogen fluoride. According to a particular embodiment of the invention there is provided a process for the production of fluoromethylhexafluoroisopropylether which comprises reacting formaldehyde with hydrogen fluoride to produce a reaction mixture containing bis(fluoromethyl) ether and contacting the said bis(fluoromethyl) ether, directly or indirectly with hexafluoroisopropyl alcohol wherein ether the molar ratio of said ether and said alcohol is in excess of 2 whereby the ether and alcohol react to produce.

BFME may be employed as is without purification and advantageously enables the operation of an integrated process including the production of BFME and its direct use as a feedstock to produce Sevoflurane. Alternatively, BFME may be treated so as to purify it partly or wholly prior to use in the process according to the invention. If desired, bis (fluoromethyl) ether may be separated from the reaction mixture and treated to produce essentially pure bis(fluoromethyl) ether which may then be reacted with hexafluoroisopropyl alcohol to produce fluoromethylhexafluoroisopropylether. In a preferred embodiment the feed stock to produce Sevoflurane comprises at least 10% by weight of BFME, more preferably at least 70% by weight of BFME and, especially, is essentially pure BFME. Optionally, formaldehyde and/or hydrogen fluoride may be fed to the process for producing Sevoflurane in addition to BFME and HFIP.

The separation, recovery and purification of Sevoflurane from product streams containing it is known and any of the known methods may be used in the process of the invention. Such methods may typically include at least one distillation step and will usually include a step of separating and recovering any by-products and/or unreacted starting materials for example bis(fluoromethyl) ether, present in the product stream. The materials recovered from the product stream can be recycled to the reaction with hexafluoroisopropyl alcohol or elsewhere as desired. In a preferred embodiment of the invention, bis(fluoromethyl) ether is recovered and recycled to the reaction step for contacting with HFIP.

The process can be operated as a batch or continuous process or a combination thereof but is preferably operated as a batch process.

A preferred embodiment of the invention includes the step of producing the bis(fluoromethyl) ether by reaction of formaldehyde (or a polymeric form of formaldehyde such as paraformaldehyde or trioxane) with hydrogen fluoride. Any of the known methods for production of the bis(fluoromethyl) ether may be employed as the ether formation step of this embodiment of the present invention. The production of bis(fluoromethyl) ether from formaldehyde and hydrogen fluoride is described, for example, in EP-A-518506 and in WO 93/10070, WO 93/12057 and WO 93/22265, for example. The disclosures of these publications are incorporated herein by reference. The ether production process described in WO 93/10070 is especially preferred and comprises reacting formaldehyde with hydrogen fluoride in a reaction distillation column from which the ether is withdrawn in essentially pure form and in particular essentially free from water.

The invention is illustrated but in now way limited by the following Examples.

EXAMPLE 1

Sevoflurane was produced and isolated in sealed PTFE test tubes. HFIP (about 16 ul) was accurately weighed into the tubes. The tubes and their contents were then cooled in an ice bath before sulphuric acid (20 ul) and BFME (100 ul) were added volumetrically with stirring. The molar reactant ratio of HFIP:BFME:$H_2SO_4$ was 1.00:9.73:2.47. The tubes were then removed from the ice bath and allowed to warm to room temperature. The contents were then stirred for 30 minutes. After this period the tubes were returned to the ice bath and the contents quenched with ice cold water (1 ml). The tube contents were then extracted with 2×0.5 ml tetrachloromethane. The extracts were combined and weighed accurately before being analysed by gas chromatography. 34 g of Sevoflurane per 100 g of HFIP were obtained.

EXAMPLE 2

The same general procedure set out in Example 1 was followed. 50 ul of HFIP was placed in the test tubes and from 100 to 200 ul of sulphuric acid and BFME was added to the tubes as set out, with the yield of Sevoflurane in Table 1.

TABLE 1

| Run # | BFME (ul) | Acid (ul) | Molar Reactant Ratio HFIP:BFME:H$_2$SO$_4$ | | | Sevoflurane (g/100 g HFIP) |
|---|---|---|---|---|---|---|
| 1 | 200 | 100 | 1.00 | 6.10 | 3.83 | 58.51 |
| 2 | 150 | 100 | 1.00 | 4.58 | 3.83 | 57.48 |
| 3 | 150 | 100 | 1.00 | 4.58 | 3.83 | 36.74 |
| 4 | 100 | 150 | 1.00 | 3.04 | 5.75 | 27.14 |
| 5 | 150 | 100 | 1.00 | 4.58 | 3.83 | 41.42 |
| 6 | 150 | 100 | 1.00 | 4.58 | 3.83 | 43.74 |
| 7 | 100 | 100 | 1.00 | 3.04 | 3.83 | 41.22 |
| 8 | 150 | 50 | 1.00 | 4.58 | 1.92 | 31.09 |
| 9 | 200 | 150 | 1.00 | 6.10 | 5.75 | 55.95 |
| 10 | 150 | 100 | 1.00 | 4.58 | 3.83 | 42.78 |
| 11 | 100 | 50 | 1.00 | 3.04 | 1.92 | 33.77 |
| 12 | 150 | 150 | 1.00 | 4.58 | 5.75 | 43.22 |
| 13 | 200 | 50 | 1.00 | 6.10 | 1.92 | 29.39 |
| 14 | 150 | 100 | 1.00 | 4.58 | 3.83 | 43.82 |
| 15 | 200 | 130 | 1.00 | 6.10 | 4.98 | 55.92 |

EXAMPLE 3

Sealed PTFE test tubes were pre-cooled in an ice bath and charged with sulphuric acid (130 ul) and BFME (200 ul). In order to control the reaction temperature a dual cell jacketed reactor system was used allowing the reaction mixture to be stirred whilst controlling the temperature to within 0.1° C. The contents of the tubes were warmed/cooled to the desired temperature. After allowing a few minutes for equilibration, 50 ul of HFIP was added in 10 ul aliquots at five minute intervals. At the end of the 20 minute addition period the contents were stirred for a further period of between 15–45 minutes. The product was isolated in accordance with the procedure set out in Example 1. The results are shown In Table 2.

TABLE 2

| Run # | Time (min) | Temperature (° C.) | Sevoflurane (g/100 g HFIP) |
|---|---|---|---|
| 1 | 15 | 22.5 | 63.42 |
| 2 | 30 | 22.5 | 64.11 |
| 3 | 30 | 22.5 | 66.74 |
| 4 | 45 | 22.5 | 76.25 |
| 5 | 30 | 15 | 53.23 |
| 6 | 30 | 30 | 91.91 |
| 7 | 30 | 22.5 | 66.26 |
| 8 | 30 | 22.5 | 60.93 |
| 9 | 45 | 30 | 89.58 |
| 10 | 45 | 15 | 57.34 |
| 11 | 30 | 22.5 | 64.02 |
| 12 | 15 | 15 | 40.59 |
| 13 | 15 | 30 | 70.48 |

EXAMPLE 4

5.6 ml (10.18 g) of 98% sulphuric acid was cooled in an ice bath with stirring and 8 ml BFME (9.51 g) was added over 14 minutes in 1 ml aliquots. This mixture was then allowed to warm over 10 minutes to room temperature, placed in a water bath at 25° C. and allowed to reach thermal equilibrium. 2 ml (3.45 g) HFIP was added to the BFME/sulphuric acid mixture at a rate of 6 ml/hr. The mixture was then maintained at 25° C. for a further 60 minutes.

The reaction mixture was then distilled at atmospheric pressure and 3.78 g of a product containing 90% Sevoflurane was obtained and analysed by gas chromatography. The yield of Sevoflurane was estimated at around 83% of the theoretical maximum.

The invention claimed is:

1. A process for the production of fluoromethylhexafluoroisopropylether which comprises contacting bis(fluoromethyl) ether with hexafluoroisopropyl alcohol wherein the molar ratio of said ether to said alcohol is in excess of 2:1 in the presence of an acid which is present in a molar ratio of 2:1 to 10:1 relative to the level of hexafluoroisopropyl alcohol whereby the ether and alcohol react to produce fluoromethylhexafluoroisopropyl ether and recovering fluoromethylhexafluoroisopropyl ether.

2. A process as claimed in claim 1 in which the molar ratio of the ether to alcohol reactants is from 3:1 to 12:1.

3. A process as claimed in any one of claim 1 or 2 in which the acid is selected from a Lewis acid and a Bronsted acid.

4. A process as claimed in claim 3 in which the acid is sulphuric acid.

5. A process as claimed in claim 1 in which the molar ratio of bis(fluoromethyl) ether to acid is less than 6:1.

6. A process as claimed in claim 5 in which the molar ratio of bis(fluoromethyl) ether to acid is less than 4:1.

7. A process as claimed in claim 6 in which hexafluoroisopropyl alcohol is added slowly to bis(fluorometyl) ether.

8. A process as claimed in claim 7 which is carried out at a temperature of less than 50° C.

9. A process as claimed in claim 8 which is carried out at a temperature of 10 to 50° C.

10. A process as claimed in claim 9 which provides a yield of fluoromethyl hexafluoroisopropyl ether of at least 30 g ether per 100 g of hexafluoroisopropyl alcohol.

11. A process for the production of fluoromethylhexafluoroisopropylether which comprises contacting bis(fluoromethyl) ether with hexafluoroisopropyl alcohol in the presence of sulphuric acid at a temperature from 10 to 50° C. wherein the molar ratio of said ether to said alcohol is from 3:1 to 12:1 the molar ratio of the acid to hexafluoroisopropyl alcohol is 2:1 to 10:1 and the molar ratio of bis(fluoromethyl) ether to acid is 4:1 to 1:2 whereby the ether and alcohol react to produce fluoromethylhexafluoroisopropylether and recovering fluoromethylhexafluoroisopropylether.

12. A process as claimed in claim 1 or claim 11 in which bis(fluoromethyl) ether is obtained by reacting formaldehyde with hydrogen fluoride to produce a reaction mixture containing bis(fluoromethyl) ether and contacting the said bis(fluoromethyl) ether, directly or indirectly with hexafluoroisopropyl alcohol to produce fluoromethylhexafluoroisopropylether.

* * * * *